United States Patent [19]

Kendall et al.

[11] Patent Number: 4,631,189
[45] Date of Patent: * Dec. 23, 1986

[54] N,N-DIMETHYLGLYCINE AND USE IN IMMUNE RESPONSE

[75] Inventors: Roger V. Kendall, New Haven, Vt.; Charles D. Graber, Charleston, S.C.

[73] Assignee: Da Vinci Laboratories, a division of FoodScience Corporation, Essex Junction, Vt.

[*] Notice: The portion of the term of this patent subsequent to May 24, 2000 has been disclaimed.

[21] Appl. No.: 722,172

[22] Filed: Apr. 9, 1985

Related U.S. Application Data

[63] Continuation of Ser. No. 469,478, Feb. 24, 1983, abandoned, which is a continuation of Ser. No. 128,781, Mar. 10, 1980, Pat. No. 4,385,068.

[51] Int. Cl.$^4$ .................. A61K 39/395; A61K 31/195
[52] U.S. Cl. ....................................... 424/85; 514/361
[58] Field of Search ................................... 424/85–92; 514/561

[56] References Cited

U.S. PATENT DOCUMENTS 2,710,876 6/1955 Krebs et al. ......................... 260/482
2,907,781 10/1959 Hermelin ............................. 424/325
3,907,869 9/1975 Bukin et al. ..................... 260/482 R Primary Examiner—Blondel Hazel
Attorney, Agent, or Firm—Sughrue, Mion, Zinn, Macpeak, and Seas

[57] ABSTRACT

N,N-dimethylglycine enhances the immune response of man and animals.

17 Claims, No Drawings

N,N-DIMETHYLGLYCINE AND USE IN IMMUNE RESPONSE

This is a continuation of application Ser. No. 469,478 filed Feb. 24, 1983, now abandoned, which is a continuation of application Ser. No. 128,781 filed Mar. 10, 1980, now U.S. Pat. No. 4,385,068.

BACKGROUND OF THE INVENTION

This invention relates to the employment of N,N-dimethylglycine to enhance the immune response of man or animals to an immunogen (vaccine) or potentiate defense mechanisms of man and animals to attack by infectious disease agents such as bacteria, viruses, fungi, protozoa or helminths (worms).

Immunization of man and animals by artifical means has several purposes. The main aim, however, is prophylactic immunization against disease, done usually by a harmless vaccine to accomplish stimulation of the immune system that otherwise might be done by uncontrolled disease with the possibility of death occurring to the host.

Prophylactic immunization to prevent clinical infection by bacteria, viruses, etc. involves production of antibody, a protein secretion of plasma cells to the vaccine administered. This antibody should preferably be long lasting, and the plasma cells, or their progeny generating it should produce more and larger quantities of the antibody to meet the challenge of the invading microorganism, when this occurs.

Also related cells, neutrophils, macrophages and lymphocytes must respond and perform phagocytosis (neutrophils and macrophages) and produce cytokines (secretions of lymphocytes and macrophages) which also inactivate, or destroy, the microorganism. The latter is referred to as cellular mediated immunity (CMI). Thus we have two limbs of the immune response.

1. Humoral (antibody) immunity produced by plasma cells;
2. Cellular Mediated (cytokines) immunity produced by macrophages and lymphocytes.

Other plasma components, such as complement, properdin, interferon, etc. are involved in the orchestration of the humoral and cellular mediated immune response of the host, but since they are not involved directly here, will not be elaborated on.

When non-viable agents are used as a vaccine, it is essential to compensate for the fact that the non-living bacteria, or their antigens are not going to elicit as good a humoral or CMI response as the living agent. Such a compensating agent is known as a immuno-adjuvant. By definition (World Health Report—Geneva, 1976) adjuvants are substances that are incorporated into, or injected simultaneously with an antigen, to potentiate non-specifically the ensuing immune response.

(In the strictest interpretation of this definition, our invention is not an adjuvant since N,N-dimethylglycine is not administered parenterally, to man or animals, along with antigen in the experiments described vide infra. It is, however, given orally, as an immunomodulator, to enhance the immunologic response; therefore, the WHO definition is broadened somewhat here, to allow the word "adjuvant" to be used.)

A great deal of research has been carried out, particularly in the Soviet Union on a substance which the Russian researchers call calcuim pangamate, (the calcium salt of pangamic acid), which has the following structure:

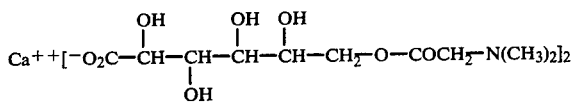

Pangamic acid may be considered to be the ester compound formed between one unit of gluconic acid and one unit of N,N-dimethylglycine. Indeed, water hydrolysis yields one molecule each of gluconic acid and N,N-dimethylglycine. This hydrolysis is illustrated below:

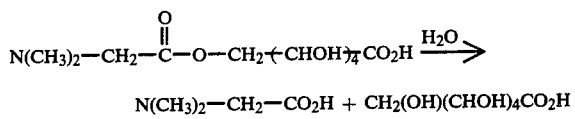

When pangamic acid is ingested, it is expected that any effect obtained which could not be attributed to pangamic acid would be the result of increased presence in the body of the expected metabolites N,N-dimethylglycine and gluconic acid, and/or further metabolic products thereof. Furthermore, it is believed that the composition of calcium pangamate used by the Russians is actually a mixture of the calcium salt of pangamic acid, calcium gluconate and N,N-dimethylglycine. It is believed that the proportion, by weight, of calcium pangamate: calcium gluconate: N,N-dimethylglycine in the Russian formulation would be about 70-75: 12.5-15: 12.5-15. In this regard, see U.S. Pat. No. 3,907,869 to Bukin et al, particularly column 2, lines 8-18. It is not certain how this composition relates to Calgam exhibited at the Montreal Expo in 1967, exported by v/o Medexport, USSR, believed to be at the present time a mixture of calcium gluconate, N-N-dimethylglycine and polymeric sugars. The inventors have reviewed extensive areas of the Russian literature on the Russian pangamic acid work, but have not found any disclosure therein believed relevant to the immuno-response enhancement effect of N,N-dimethylglycine as claimed herein. See "Effectiveness of Calcuim Pangamate Introduced to Vaccinated and Irradiated Animals" by Nizametdinova in *Reports of the Kazan Veterinary Institute* Vol 112, pp 100-104 (1972) where calcium pangamate is described as being injected into animals which have been vaccinated and then irradiated at a dosage sufficient to cause radiation sickness. The Russian workers conclude that the immunized and subsequently irradiated animals exhibited a normalization of immunological activity following calcium pangamate administration, as compared to a control group, which did not. It is interesting to note that although the Russians in one experiment are stated to have included a test group of animals which were vaccinated and then injected with calcium pangamate (not irradiated), no data thereof is disclosed. Thus, no information on calcium pangamate potentiation of the normal immune response is proffered. The present invention is not concerned with treatment of radiation sickness in irradiated animals but enhancing the natural immuno response of a living organism.

U.S. Pat. No. 3,392,195 to Galat discloses the use of glycine as an antacid.

U.S. Pat. No. 2,907,781 to Hermelin discloses the use of an aluminum salt of glycine in treatment of stomach ulcers.

U.S. Pat. No. 3,167,475 to Gottfried et al relates to the use of an alcohol derivative of N,N-dimethylglycine in the treatment of allergies.

U.S. Pat. No. 2,710,876 to Krebs et al discloses the reaction of N,N-dimethylglycine with gluconic acid to yield pangamic acid.

The non-Russian literature is replete with articles concerning N,N-dimethylglycine's participation in metabolic processes, particularly the 1-carbon cycle involving choline and betaine. Betaine yields N,N-dimethylglycine after transferring one methyl group to homocysteine, (see *Principles of Biochemistry*, White et al, McGraw-Hill, 6th Ed. 1978, p. 695.) However, the literature reviewed by the present inventors does not relate to the immuno response characteristics now found for N,N-dimethylglycine.

Lastly, some of the work on which the present invention is based is disclosed in *B-15: The "Miracle Vitamin"* by Brenda Forman (Fred Jordan Books/Grosset and Dunlap, New York, 1979—See pages 149-151) and was reported in the Proceedings of the Annual Meeting of the American Society for Microbiology, Southeastern and South Carolina Branches, Atlanta, Ga., Nov. 8-9, 1979.

SUMMARY OF THE INVENTION

It is an object of this invention to provide a method to enhance the natural immunological response of the body.

It is another object of this invention to provide a method to enhance one or both of the cell-mediated response and humoral response of the body.

Still another object of this invention is to provide a method whereby the deliberately induced production of antibody (artifically acquired) in a living organism can be enhanced.

A further object of this invention is to provide a method to increase the amount of antibody production and/or decrease the time of antibody production in the deliberate induced (artifically acquired, i.e. vaccine) production of antibody in a living organism.

The above and other objects of the present invention are obtained by administering N,N-dimethylglycine to a living organism in an amount sufficient to enhance the immunological response of the living organism. In a preferred embodiment of the present invention the living organism is a mammal. In another preferred embodiment of the present invention, the N,N-dimethylglycine is administered in an amount sufficient to enhance both of the cell mediated and humoral immune response systems.

In still another preferred embodiment of the invention, the N,N-dimethylglycine is administered to laboratory animals being stimulated to produce antibodies to increase the level of antibody production and/or decrease the time necessary for a given antibody level recovery. (Anamnestic response or booster response to a second injection of immunogen.)

In certain aspects of the present invention the N,N-dimethylglycine is administered in a maintenance dosage to the living organism so that the immunological response of the living organism is potentiated when exposed to an antigen in a natural environment and/or when deliberately exposed.

In another aspect of the present invention, the N,N-dimethylglycine is administered after man or a lower animal has been exposed to a disease agent having an antigenic component in a natural environment in order to aid the host in responding to the naturally occuring infection.

DETAILED DESCRIPTION OF THE INVENTION

As noted hereinbefore, N,N-dimethylglycine,

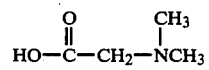

is believed to be an active metabolite of the calcium pangamate investigated so extensively by the Russians and/or an actual component of the Russian formulation which is available in the Soviet Union and was exhibited at Montreal Expo 1967. Now, we have found that N,N-dimethylglycine has positive effects on the immune response system. Thus, the present invention has two broad aspects. One broad aspect is the use of N,N-dimethylglycine to facilitate recoverable antibody production in a living host, which always is a mammal. The second broad aspect of the present invention involves administration of N,N-dimethylglycine to a living host, most usually a higher mammal, or human, to aid the host in combatting a naturally occuring infection by enhanced humoral or cellular mediated immunity and/or to aid in responding to vaccine to build up resistance. In this general aspect administration could be before or after infection.

In the first broad aspect of the present invention as above mentioned, as immunogen, such as bacteria, virus, toxin, etc., is deliberately injected into an animal to illicit antibody production. A conventional method, such as *PROC. SOC. EXP. BIOL. MED.* 128, 347 (1968) is employed and then the antibodies formed in the living host are collected.

The host used for antibody production and collection is usually a mammal such as cattle, oxen, guinea pigs, horses, rabbits, etc.

On preparing antibodies, a predetermined amount of antigen is diluted with physiological saline solution to a predetermined concentration, say 0.5 to 2 mg per ml. This solution is then mixed with conventional adjuvant such as Complete Freund's adjuvant, to prepare a dispersion, which is then injected into the host. For example, rabbits are often employed and injected intradermally. Small amounts of the antigen are used, say 0.5 to 2 mg, at a time, with repeating the dosage periodically, say about once every two weeks, over a period of up to two or three months.

Collection of antibodies can be performed by bleeding the immunized animal after the last administration of the adjuvant-immunogen, usually one to two weeks after last administration, and centrifuging the blood thus obtained to separate antiserum (antibody).

The above antibody preparation procedure illustrates the type of method where the present invention would be used in increasing the antibody production.

Example 1 illustrates the influence of N,N-dimethylglycine on the humoral response of the rabbit to typhoid vaccine. Example 2 demonstrates the influence of N,N-dimethylglycine on both humoral and cell mediated immunity in humans.

EXAMPLE 1

Twelve New Zealand white rabbits of approximately two kilo weight each were randomly assigned as six test and six control animals. All rabbits were fed standard pellet feed with ad lib watering plus a formulation approximately consisting of 30 milligrams calcium gluconate and 20 milligrams N,N-dimethylglycine HCl per kilo weight of rabbit being administered per os to all six test rabbits daily. Force feeding was done daily with a specially contrived syringe starting 15 days prior to immunization of animals and continuing through the duration of the experiment. Bleeding (3 milliliters) was done prior to and at the conclusion of the experiment (after 10 days) from the marginal vein of the ear.

Typhoid Vaccine (Wyeth Laboratories) which includes Vi, O and H antigens was administered to all rabbits on day zero (0.2 ml intradermally) and on day ten (0.2 ml intramuscularly).

Agglutinin of O (Lipopolysaccharide antigen) and H (flagellin, protein antigen) was done at the end of the experiment using standard techniques. The test T of Significance was used for analyses of data.

RESULTS

All animals (test and control) gained an average of 0.8 pounds per rabbit during the experiment. One test animal died of coccidiosis during the experiment.

TABLE 1

Pre and Post O Antibody Titer in Test and Control Rabbits

Pre Mean O titer for test rabbits, 1:16
Post Mean O titer for test rabbits, 1:1024
Pre Mean O titer for control rabbits, 1:53
Post Mean O for titer for control rabbits, 1:853

From the above it can be seen that not only was there a higher mean humoral response (not significant) between groups to O antigen in test rabbits (1:1024 to 1:853) but also a higher general response over pre-immunologic titers in test rabbits over controls 1024 1 to 16 and 853 to 53.

TABLE 2

Pre and Post H Antibody Titer in Test and Control Rabbits

Pre Mean H titer for test rabbits, 0
Post Mean H titer for test rabbits, 269
Pre Mean H titer for control rabbits, 4
Post Mean H titer for control rabbits, 53

Again the test animals overall response is greater within the groups in favor of the test animals 269 versus 14 and significantly there is a five fold increase of test animal post mean antibody titer over control animal post mean antibody titer. This is significant at the 5 percent level.

The above results suggest improved humoral response to immunogen in the N,N-dimethylglycine fed animals. Particularly remarkable was the H antigen response in test animals as compared to that of controls. H is a protein flagellar antigen and would be expected to show short term rise differences if they were to occur. The LPS (Lipo Polysaccharide) O antigen gave good titers but only slight overall total differences.

Thus humoral response was better with both O and H antigens. The animals were receiving approximately 15 times the recommended dietary supplement for humans to force the appearance of immunologic differences, although at a dose calculated to be well below any possible toxic effect. Of course, it is also possible that the optimum dosage of N,N-dimethylglycine to elicit maximum response may be different than that recommended at the present invention for use as a general dietary supplement.

While the above experiment was carried out, a study of cellular mediated response in animals gave inconclusive results to Varidase (Lederle's Streptodoranse-Streptokinase enzyme which detects cell mediated response through skin testing), used for this purpose.

EXAMPLE 2

Twenty human volunteers representing an age span of 14 to 64 years were the test and control subjects used. All were immunized with 0.5 ml. Pneumovax (pneumococcal vaccine used to protect humans against this type pneumonia) at an appropriate period during the experiment. Ten test subjects (5 male 5 female) were given 2 tablets containing together approximately 40 mg of N,N-dimethylglycine HCl and 61.5 mg calcium gluconate three times a day, orally, starting two weeks prior to immunization and for 56 days thereafter. Ten control subjects (5 males—5 females; age matched to correspond to test individuals) received instead 2 placebo tablets containing together approximately 100 mg of calcium gluconate three times a day for the same period. (For instance, several husband and wife teams were used and were randomly assigned to a double blind study, the idea being that similar age, similar diet, would minimize unusual pairing variables).

On day 0, 14, 35 and 56, blood was drawn in an amount of 30 ml. from all of the 20 subjects, to permit studies of serum hemagglutinin (antibody) to pneumovax polysaccharide, an antigen injected on day 14 as previously stated, to all subjects.

Similarly, the white cells of the blood obtained were used to study the lymphocyte inhibition factor (LIF) produced by all patients in response to Concanavalin A, Varidase, and the pneumovax antigen used to stimulate these cells.

It would be expected if N,N-dimethylglycine was a useful immunologic adjuvant or immunologic enhancer of humoral and cellular mediated immunity, that the test group would show significant differences in favor of the test group over controls.

This is exactly what happened in the 10 test subjects given N,N-dimethylglycine with regard to their antibody response.

Table 1 shows a 19.2 mean antibody titer for test subjects (N,N-dimethylglycine treated) as compared to the control (placebo) mean antibody titer of 4.3. This is more than a 4-fold difference usually regarded as imperative to diagnostic serologic significance and was significant at a P value of less than 1% when assessed by repeated measured analyses of variance at log 10.

TABLE 1

| TEST AND CONTROL AVERAGE PRE AND POST TITER DIFFERENCES. | | |
|---|---|---|
| PRE (AVE) | POST (AVE) | TITER DIFFERENCE |
| TEST 10 (5 Females and 5 Males) 46.2 | 889.6 | 19.2 |
| CONTROLS 31.1 | 136.4 | 4.3 |

TABLE 1-continued

TEST AND CONTROL AVERAGE PRE AND POST TITER DIFFERENCES.

| | PRE (AVE) | POST (AVE) | TITER DIFFERENCE |
|---|---|---|---|
| 10 (6 Females and 4 Males) | | | |

P < 0.01
(Repeated Measures Analysis of variance at log 10)

The LIF studies also were significantly different in favor of the test group (N,N-dimethylglycine-fed), as opposed to controls (placebo-fed). Table 2 shows no significant change for Con A, but for Varidase stimulated lymphocytes there was a significant difference at 14 days (0.85 vs. 0.97) in favor of the test group (P<0.025). At the end of the experiment, the difference was even more significant (0.79 vs. 0.95) in favor of the test group (P<0.001).

Of great interest is the LIF response to pneumavox. The latter is a 'B' cell stimulator, and it was not expected that T cells, which provide the LIF response, would respond to produce the inhibition that was noted.

At 35 days, test group lymphocytes produced average zones of 0.79 vs 0.92 for controls, significant at less than 0.01% and again at day 56, the difference was equally marked and significant, 0.81 vs. 0.94, and again a P value of less than 1/10 of 1%.

This human volunteer experiment thus shows N,N-dimethylglycine to be an immune modulator, enhancer or adjuvant for both limbs of the immune response (humoral and cellular mediated). This is unique. It means that N,N-dimethylglycine represents in appropriate dosage (120 mg/day) a non-toxic stimulator of total host resistance, presumably capable of protecting against agents of infection and disease.

TABLE 2

TEST AND CONTROL LIF VALUES (MMI) FOR CON A, VARIDASE AND PNEUMOVAX STIMULATED LYMPHOCYTES

| DAYS | 0 | 14 | 35 | 56 |
|---|---|---|---|---|
| D+ | 0.63 | 0.70 | 0.67 | 0.68 |
| CON A | ±0.05 | ±0.06 | ±0.05 | ±0.01 |
| 9 mcgm | N.S.(a) | N.S. | N.S. | N.S. |
| D− | 0.66 | 0.66 | 0.69 | 0.67 |
| | ±0.05 | ±0.04 | ±0.05 | ±0.04 |
| D+ | 0.95 | 0.85 | 0.87 | 0.79 |
| | ±0.05 | ±0.06(b) | ±0.03 | ±0.04(b) |
| SK-SD (Varidase) | N.S. | <0.025 | N.S. | <0.001 |
| 2.5 units/ml | 0.92 | 0.97 | 0.90 | 0.95 |
| D− | ±0.08 | ±0.05 | ±0.06 | ±0.08 |
| D+ | 0.96 | 1.06 | 0.79 | 0.81 |
| | ±0.06 | ±0.09 | ±0.01(b) | ±0.08(b) |
| PNEUMOVAX | N.S. | N.S. | <0.001 | <0.001 |
| 14 mcgm/ml. | 0.98 | 0.96 | 0.92 | 0.94 |
| D− | ±0.04 | ±0.07 | ±0.01 | ±0.06 |

D+ = Dimethylglycine - fed (test group)
D− = Placebo fed (control group)
(a)N.S. means non-significant
(b)T test significant The N,N-dimethylglycine will most usually be administered orally in tablet formulations, although liquids for oral administration and injectable forms are contemplated, particularly injections where antibody production in animals is being effected.

Since N,N-dimethylglycine is essentially non-toxic, it is contemplated that dosages can vary from about 0.05 to 15 mg/Kg/day, preferably about 0.1 to 5 mg/KG/day, most preferably about 1.0 to 1.5 mg/Kg/day based on free N,N-dimethylglycine. Where the N,N-dimethylgylcine is being used to aid the body in combatting a specific acute infection, higher short term dosages may be indicated. The N,N-dimethylglycine can be used as such or as a pharmaceutically acceptable salt thereof. Acid addition salts such as the HCl, HBr, sulfate or tartrate salts, or base addition salts such as the calcium, magnesium or barium salts, can be employed.

The compositions used in the present invention can consist of N,N-dimethylglycine or N,N-dimethylglycine plus other active components. Quite often, the N,N-dimethylglycine is administered with calcium gluconate. Vitamins and minerals and other dietary additives can be used in formulating an overall maintenance level product. Various conventional pharmaceutically acceptable carriers will be employed in forming unit dosage forms.

Variations of the invention will be apparent to the skilled artisan.

We claim:

1. A process for enhancing the natural immunological response of a human which comprises orally administering N,N-dimethylglycine or a pharmaceutically acceptable salt thereof to the human in an amount effective to enhance the immunological response of such human.

2. The process of claim 1 wherein the cell-mediated immunological response, the humoral immunological response or both the cell-mediated and humoral immunological responses are enhanced.

3. The process of claim 1 wherein the human is being used to produce antibody for collection.

4. The process of claim 3 wherein the N,N-dimethylglycine or pharmaceutically acceptable salt thereof is administered in an amount effective to accomplish at least one of increasing the amount of antibody products and decreasing the time to reach a given level of antibody production expected in said human.

5. The process of claim 1 or 2 wherein the N,N-dimethylglycine or pharmaceutically acceptable salt thereof is administered before, after or with an antigenic substance to the human.

6. The process of claim 1 or 2 wherein the N,N-dimethylglycine or pharmaceutically acceptable salt thereof is administered to aid the human in combatting an infectious disease agent selected from the group consisting of bacteria, viruses, fungi, protozoa and helminths.

7. The process of claim 1 or 2 wherein the N,N-dimethylglycine or pharmaceutically acceptable salt thereof is administered to aid the living organism in developing a resistance or immunity to a potential infective agent selected from the group consisting of bacteria, viruses, fungi, protozoa and helminths.

8. The process of claim 1 or 2 wherein the N,N-dimethylglycine or pharmaceutically acceptable salt thereof is administered in a preventive maintenance regimen.

9. The process of claim 1 or 2 wherein the N,N-dimethylglycine or pharmaceutically acceptable salt thereof is administered within a dosage range of about 0.05 mg/kg/day to 15 mg/kg/day based on free N,N-dimethylglycine.

10. The process of claims 1 or 2 wherein the N,N-dimethylglycine or pharmaceutically acceptable salt thereof is administered in conjunction with at least one of vitamins, minerals and non-fuel nutrients.

11. The process of claims 1 or 2 wherein the N,N-dimethylglycine or pharmaceutically acceptable salt thereof is administered within a dosage range of about 0.1 mg/Kg/day to 5.0 mg/Kg/day based on free N,N-di-methylglycine.

12. The process of claims 1 or 2 wherein the N,N-dimethylglycine pharmaceutically acceptable salt thereof is administered within a dosage range of about 1.0 mg/Kg/day to 1.5 mg/Kg/day based on free N,N-di-methylglycine.

13. A process for producing and collecting antibody which comprises administering an antigenic substance to a non-radiation sick lower animal, administering N,N-dimethylglycine or a pharmaceutically acceptable salt thereof to the lower animal before, with or after the antigenic substance in an amount effective to enhance the immunological response of said animal to the antigenic substance and collecting antibody produced by said animal in response to said antigenic substance.

14. The process of claim 13 wherein the N,N-dimethylglycine or pharmaceutically acceptable salt thereof is administered in an amount effective to increase the amount of antibody products or to decrease the time to reach a given level of antibody production expected in said lower animal.

15. The process of claim 13 wherein the N,N-dimethylglycine or pharmaceutically acceptable salt thereof is administered within a dosage range of about 0.05 mg/kg/day to 15 mg/kg/day based on free N,N-dimethylglycine.

16. The process of claim 13 wherein the N,N-dimethylglycine or pharmaceutically acceptable salt thereof is administered within a dosage range of about 0.1 mg/Kg/day to 5.0 mg/Kg/day based on free N,N-dimethylglycine.

17. The process of claim 13 wherein the N,N-dimethylglycine or pharmaceutically acceptable salt thereof is administered within a dosage range of about 1.0 mg/Kg/day to 1.5 mg/Kg/day based on free N,N-dimethylglycine.

* * * * *